United States Patent [19]

Amselem

[11] 3,983,125

[45] Sept. 28, 1976

[54] THIENO-PYRIDINE DERIVATIVES, PROCESS FOR THEIR PREPARATION AND THEIR APPLICATIONS

[75] Inventor: Armand Amselem, Toulouse, France

[73] Assignee: Parcor, Paris, France

[22] Filed: July 3, 1975

[21] Appl. No.: 593,051

[30] Foreign Application Priority Data
July 16, 1974 France .............................. 74.24631
June 5, 1975 France .............................. 75.17552

[52] U.S. Cl. ......................... 260/294.8 C; 424/263
[51] Int. Cl.² ....................................... C07D 213/28
[58] Field of Search ............... 260/294.8 C; 424/263

[56] References Cited
UNITED STATES PATENTS
3,845,065  10/1974  Shen et al. ................... 260/294.8 C

*Primary Examiner*—Alan L. Rotman
*Attorney, Agent, or Firm*—Young & Thompson

[57] ABSTRACT

This invention relates to thieno-pyridine derivatives which may be represented by either one of the following formulae:

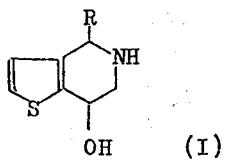

(I) 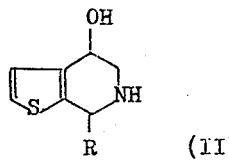 (II)

in which R is hydrogen or an alkyl radical having 1–6 carbon atoms, and their acid addition salts with inorganic or organic acids.

Said derivatives have anti-inflammatory, antalgic and blood-platelet aggregation-inhibiting activity in mice and rats. In addition, they may also be used as intermediates in the synthesis of a large number of derivatives used both in the chemical and pharmaceutical industries.

10 Claims, No Drawings

THIENO-PYRIDINE DERIVATIVES, PROCESS FOR THEIR PREPARATION AND THEIR APPLICATIONS

This invention relates to thieno-pyridine derivatives which may be represented by either one of the following formulae:

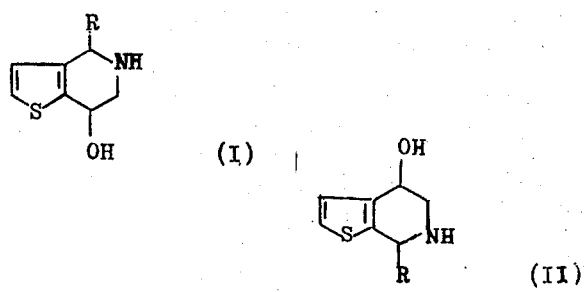

in which R represents a hydrogen atom or an alkyl radical having 1-6 carbon atoms, and their acid addition salts with inorganic or organic acids.

Said derivatives have anti-inflammatory, antalgic and blood-platelet aggregation-inhibiting activity in mice and rats. In addition, they may also be used as intermediates in the synthesis of a large number of derivatives used both in the chemical and pharmaceutical industries.

The invention relates also to a process for the preparation of the above-defined compounds, comprising cyclizing a N-[2,2-(OX)$_2$]ethyl-α,α'-[(3-thienyl)alkyl]methylamine of the formula (III) or a N-[2,2-(OX)$_2$]ethyl-α,α'-[(2-thienyl)-alkyl]methylamine of the formula (IV) in which X is a lower alkyl group or both the X groups form together a 2- or 3-membered alkylene radical, by treatment with hydrochloric acid, the desired compounds being obtained as the hydrochlorides. The reaction scheme of the process for the preparation of said compounds is as follows:

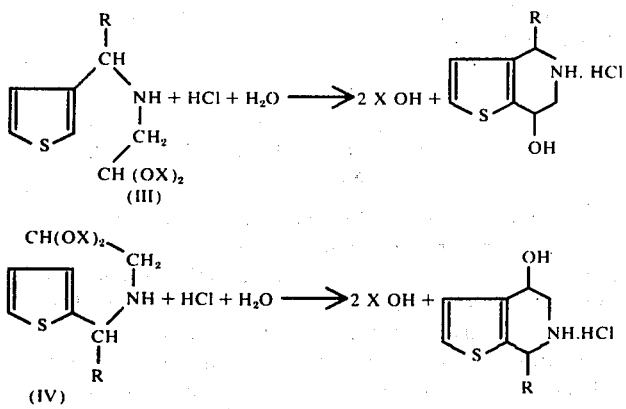

The free base may be obtained by neutralizing an aqueous solution of the derivative with a base such as sodium hydroxide (NaOH) or ammonia (NH$_4$OH) with subsequent extraction with an organic solvent such as ether, for example.

Intermediate compounds of the formulae (III) and (IV) are themselves obtained by hydrogenation of the Schiff base formed between a 3-acyl-thiophene or a 2-acyl-thiophene and the acetal of the corresponding aminoacetaldehyde:

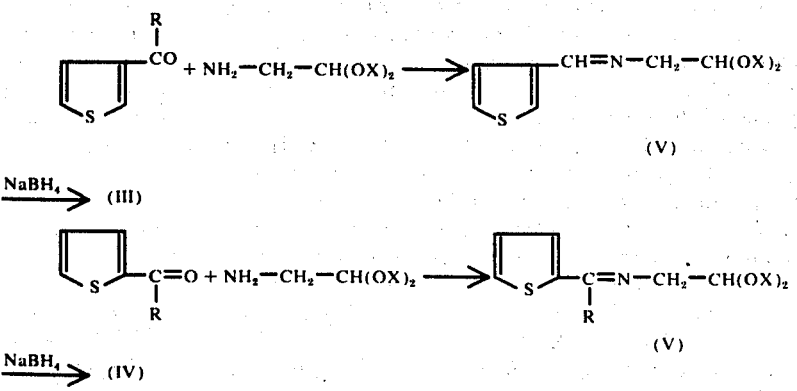

As hydrogenating agent, there is advantageously used a reducing derivative such as an alkali metal borohydride, e.g., sodium borohydride.

The cyclization reaction which produces the desired compounds of the formula (I) or (II) is conducted by treatment with a concentrated strong inorganic acid, such as hydrochloric acid, for example.

The reaction is conducted at room temperature, with constant stirring and may last from a few hours to several days.

The aminoacetals condensed with thienaldehyde may be derived from a variety of alcohols: thus, the group $—CH(OX)_2$, in which X has the above-defined meaning, may be, typically:

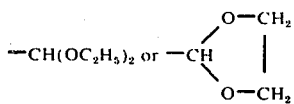

The following non-limiting examples are given to illustrate the preparation of the compounds according to the invention

EXAMPLE 1

Preparation of
7-hydroxy-4,5,6,7-tetrahydro-thieno[3,2-c]pyridine
(Derivative 1)

Into a flask provided with a Dean-Stark water-separator and an ascending cooler are added 22.4 g (0.2 mole) 3-thienaldehyde, 23.1 g (0.2 mole) aminoacetaldehyde dimethyl acetal and 45 ml benzene. The mixture is refluxed during 1.5 hours, until the theoretical amount of water formed in the reaction has been collected. Evaporation of the benzene and distillation of the residual oil give 38.2 g of Schiff base having the formula (V) (Yield: 96%. B.p./0.1 mm Hg = 86°–90°C).

43.8 g (0.2 mole) of the compound of the formula (V) are dissolved in 185 ml ethanol and 12.5 g (0.33 mole) sodium borohydride $NaBH_4$ are then added portionwise to this solution. The mixture is left aside at room temperature during one hour and is then refluxed during one hour. The alcohol is evaporated off in vacuo and the residue is taken up into 250 ml of a 20% aqueous acetic acid solution. The resulting solution is washed with ether; it is then made alkaline by addition of ammonia and again extracted with ether. The ether fractions are combined, dried over sodium sulfate and then concentrated in vacuo, to give 31.4 g (Yield: 71%) of an oily residue comprising the amino compound of the formula (III).

A mixture of the aminoacetal of the formula (III) (5 g) and 6N hydrochloric acid (100 ml) is stirred at room temperature during 20 hours. After evaporation in vacuo, at 40°C, the solid residue is taken up into ether, filtered and washed with ether, after which it is dried, to give 4.1 g (Yield: 86%) of the hydrochloride of the derivative of the formula (I) which has a melting point (Kofler block) of 205°C.

The corresponding base may be obtained by neutralization of an aqueous solution of the resulting derivative with ammonia and extraction with ether. Evaporation of the ether gives a solid which has a melting point (Kofler block) of 122°C.

EXAMPLE 2

Preparation of
4-hydroxy-4,5,6,7-tetrahydro-thieno[2,3-c]pyridine
(Derivative 2)

Using the same procedure, but starting from 2-thienaldehyde, there is obtained the hydrochloride of the desired derivative which has a melting point (Kofler block) of 203°C.

EXAMPLE 3

Preparation of
4-hydroxy-7-methyl-4,5,6,7-tetrahydro-thieno[2,3-c]pyridine (Formula (II); $R = CH_3$) (Derivative 3)

Into a flask provided with a water-separator with overhead cooler, are added 100 g (0.794 mole) 2-acetyl-thiophene, 91 g (0.87 mole) aminoacetaldehyde dimethylacetal and 250 ml toluene. The mixture is refluxed during 48 hours and is then concentrated in vacuo. The residual oil, after vacuum distillation, gives 111 g Schiff base (Yield: 66%. B.p./0.05 mm Hg = 88°–90°C). 110 g of the preceding compound are dissolved in 600 ml ethanol and 29.6 g (0.567 mole) sodium borohydride are then added thereto portionwise. The mixture is stirred during 1.5 hour at room temperature and is then refluxed during 5 hours. The alcohol is evaporated off in vacuo and the residue is made acidic with a 20% aqueous acetic acid solution.

The resulting solution is washed with ether; it is then made alkaline by addition of ammonia and is extracted with methylene chloride. The methylene chloride fractions are combined, dried over sodium sulfate and then concentrated in vacuo. Distillation of the residual oil gives 84 g of the desired aminoacetal (Yield: 76%. B.p./0.1 mm Hg = 70°–74°C).

A mixture of 56 g of the previously obtained aminoacetal and 330 ml of 6N hydrochloric acid is stirred at room temperature during 80 hours. After evaporation in vacuo at 40°C, the residue is taken up into acetone, filtered and then washed with acetone. The resulting material is then dried, to give 32.4 g (Yield: 74%) 4-hydroxy-7-methyl-4,5,6,7-tetrahydro-thieno[2,3-c]pyridine hydrochloride, m.p. (Kofler block) = 240°–244°C.

EXAMPLE 4

Preparation of
7-ethyl-4-hydroxy-4,5,6,7-tetrahydro-thieno[2,3-c]pyridine (Formula (II); $R = C_2H_5$) (Derivative 4)

Using the same procedure as in Example 3, but starting from 2-propionyl thiophene, there is obtained the hydrochloride of the desired derivative which, after treatment with sodium hydroxide, gives the base. The latter is in turn converted to the hemi-oxalate hydrate which has a melting point (Kofler block) of 208°–210°C.

EXAMPLE 5

Preparation of
7-hydroxy-4-methyl-4,5,6,7-tetrahydro-thieno[3,2-c]pyridine (Formula (I); $R = CH_3$) (Derivative 5)

Using the same procedure as in Example 3, but starting from 3-acetyl thiophene, there is obtained the hydrochloride of the desired derivative which has a melting point (Kofler block) of 222°–228°C.

EXAMPLE 6

Preparation of
4-ethyl-7-hydroxy-4,5,6,7-tetrahydro-thieno[3,2-c]pyridine (Formula (I); $R = C_2H_5$) (Derivative 6)

Using the same procedure as in Example 3, but starting from 3-propionyl thiophene, there is obtained the hydrochloride of the desired derivative which has a melting point (Kofler block) of 190°–198°C.

The results of toxicological and pharmacological investigation reported hereinbelow provide evidence of the interesting activities of the derivatives according to the present invention, in particular their anti-inflammatory, antalgic and blood-platelet aggregation-inhibiting activities.

TOXICOLOGICAL INVESTIGATION

This investigation has demonstrated the low toxicity and the good tolerance of the derivatives of this invention.

For indicative purposes, the $LD_{50}/24$ hrs/kg body weight, determined in mice by the intravenous route according to the method disclosed by Miller and Tainter, is 75 mg with Derivative $n°1$, 68 mg with Derivative $n°2$, 300 mg with Derivative $n°3$, 285 mg with Derivative $n°4$, 155 mg with Derivative $n°5$ and 210 mg with Derivative $n°6$.

By the oral route, the $LD_{50}/24$ hrs/kg body weight is in excess of 300 mg with derivatives $n°1$ and $n°2$.

The chronic or delayed toxicity tests have shown the good tolerance of the derivatives of the present invention which never induced any local or systemic reaction nor any perturbation in the regularly effected biological control tests.

PHARMACOLOGICAL INVESTIGATION

The pharmacological tests show that the derivatives of the present invention exhibit anti-inflammatory, antalgic and blood-platelet aggregation inhibiting activities.

1. Anti-inflammatory action a. Carrageenin-induced localized edema method

A 1% carrageenin solution (0.1 ml) is injected in the metatarsal flexor muscles of the right posterior limb of a rat at time 0 (zero). The animals of the treated lot are additionally given orally 100 mg/kg of the respective test derivatives, one hour prior to and then simultaneously with the injection of the phlogogenic agent, and then one hour and 2.5 hours thereafter. The determinations effected by means of a ROCH micrometer at times 0, 1 hour, 2 hours, 3 hours and 5 hours after carrageenin administration, provide a measure of the percent anti-inflammatory activity, as a function of time. The resulting data are reported in following Table I.

TABLE I

| Derivative No. | Percent anti-inflammatory activity | | |
|---|---|---|---|
| | after 1 hour | after 2 hours | after 5 hours |
| 1 | 41 | 48 | 53 |
| 2 | 43 | 54 | 58 |
| 3 | 38 | 47 | 56 |
| 4 | 43 | 51 | 59 |
| 5 | 41 | 55 | 60 |
| 6 | 39 | 51 | 57 | b. Ovalbumin-induced systemic edema method

Rats are administered a simultaneous intraperitoneal injection of 1 ml ovalbumin and 0.5 ml of a 1% aqueous Evans Blue solution. On the other hand, the animals of the treated lot are administered orally 100 mg/kg of the test derivative, one hour prior to and simultaneously with the ovalbumin administration. The determinations are effected after 2 hours and after 3 hours. Thus are determined the average intensity of the edema and the percent decrease of the edematous reaction with respect to the controls. Said percentages are set forth in following Table II.

TABLE II

| Derivative No. | Percent decrease | |
|---|---|---|
| | After two hours | After three hours |
| 1 | 54 | 58 |
| 2 | 56 | 65 |
| 3 | 45 | 56 |
| 4 | 54 | 62 |
| 5 | 52 | 64 |
| 6 | 49 | 64 |

2. Antalgic action a. Acetic acid method, according to Koster, Anderson and de Beer (Fed. Proced., 18, 1959, 412, 1, 626).

Intraperitoneal injection of a dilute acetic acid solution produces, in mice, characteristic repeated writhing movements, under the influence of pain.

Oral administration of the derivatives of this invention to the animals of the treated lot, at a dosage of 100 mg/kg, 30 minutes prior to the intraperitoneal injection of acetic acid, shows that, with respect to the untreated reference lot, the number of writhing movements is markedly decreased within the following 30 minutes.

The percent antalgic activity thus determined is 63% with derivative $n°1$, 66% with derivative $n°2$, 55% with derivative $n°3$, 61% with derivative $n°4$, 59% with derivative $n°5$ and 58% with derivative $n°6$.

b. Mechanical stimulation method according to Haffner (Deutsch. Wisch., 1959, 55, 731–733)

This method comprises placing a forcipressure forceps at the base of the tail of a mouse and noting the number of self-inflicted bites due to the animal's efforts to remove the forceps. The decrease of the number of bites prior to and after oral administration of the test derivative, at a dosage of 100 mg/kg, provides a measure of the antalgic activity of the derivatives of this invention. The mean percent antalgic activity thus determined as a function of time is reported in following Table III.

TABLE III

| Derivative No. | Average percent antalgic activity | | | |
|---|---|---|---|---|
| | after 30 min. | after 1 hr | after 2 hrs | after 3 hrs |
| 1 | 72 | 68 | 62 | 55 |
| 2 | 76 | 69 | 60 | 54 |
| 3 | 68 | 62 | 58 | 50 |
| 4 | 74 | 65 | 60 | 52 |
| 5 | 76 | 64 | 61 | 52 |
| 6 | 71 | 67 | 63 | 58 |

3. Inhibiting action on blood-platelet aggregation

Rat serum having a high content in blood-platelets is normally cloudy. It is clarified by addition of adenosine diphosphate which causes aggregation of the blood-platelets. When the same test is effected with serum taken from an animal which has been administered 100 mg/kg of a derivative that possesses an inhibiting activity on blood-platelet aggregation, aggregation of the blood-platelets does not occur and the serum remains cloudy. Thus, the inhibiting capacity of the test derivatives on blood-platelet aggregation may be determined by means of a simple spectrophotometric turbidimetric determination.

The tests are carried out with lots of five rats for each derivatives (3 control animals and 2 treated animals). Thus, it is found that the derivatives according to the present invention protect the animals against blood-platelet aggregation to an extent of more than 90%.

It is apparent from the toxicological and pharmacological investigations reported above that the derivatives of this invention possess good tolerance characteristics and that they possess anti-inflammatory and antalgic activities and also an inhibiting activity on blood-platelet aggregation.

Therefore, the invention contemplates also within its scope a therapeutic composition comprising, as active ingredient, a derivative of aforementioned formula (I) or (II) or an acid addition salt thereof with a pharmaceutically acceptable acid.

The composition according to the present invention may be formulated, for oral administration, as tablets, coated tablets, capsules, drops and syrups. It may also be formulated, for rectal administration, as suppositories and, for parenteral administration, as injectable solutions.

Each unit dose contains advantageously from 0.025 g to 0.500 g active ingredient, and the daily dosage regimen may vary within a range from 0.025 g to 1 g active ingredient.

Non limiting examples of pharmaceutical formulations of the composition of this invention are given hereinafter.

EXAMPLE 7 - Coated tablets

| | | |
|---|---|---|
| CORE | (Derivative No. 3 | 0.075 g |
| | (Talc | 0.010 g |
| | (Wheat starch | 0.025 g |
| | (Lactose | 0.005 g |
| | (Magnesium stearate | 0.005 g |
| COATING | (Stearic acid | 0.005 g |
| | (Talc | 0.010 g |
| | (Potato starch | 0.015 g |
| | (Gum arabic | 0.005 g |
| | (Gelatin | 0.002 g |
| | (White wax | 0.001 g |
| | (Carnauba wax | 0.001 g |
| | (Sucrose q.s. to make one coated tablet | |

EXAMPLE 8 - Tablets

| | |
|---|---|
| Derivative No. 4 | 0.100 g |
| Talc | 0.005 g |
| Lactose | 0.025 g |
| Magnesium stearate | 0.025 g |
| Stearic acid | 0.002 g |

EXAMPLE 9 - Capsules

| | |
|---|---|
| Derivative No. 5 | 0.150 g |
| Magnesium stearate | 0.010 g |
| Talc | 0.005 g |

EXAMPLE 10 - Drops

| | |
|---|---|
| Derivative No. 6 | 2.50 g |
| Flavoured excipient, q.s. to make | 30 ml |

EXAMPLE 11 - Injectable solution

| | |
|---|---|
| Derivative No. 4 | 0.100 g |
| Isotonic solution | 3 ml |

EXAMPLE 12 - Coated tablets

| | | |
|---|---|---|
| CORE | (Derivative No. 1 | 0.075 g |
| | (Talc | 0.010 g |
| | (Alginic acid | 0.010 g |
| | (Wheat starch | 0.025 g |
| | (Shellac | 0.005 g |
| | (Magnesium stearate | 0.005 g |
| COATING | (Talc | 0.010 g |
| | (Wheat starch | 0.015 g |
| | (Gum arabic | 0.005 g |
| | (Gelatin | 0.002 g |
| | (White wax | 0.001 g |
| | (Carnauba wax | 0.001 g |
| | (Sucrose q.s. to make 1 coated tablet | |

EXAMPLE 13 - Tablets

| | |
|---|---|
| Derivative No. 2 | 0.100 g |
| Talc | 0.010 g |
| Lactose | 0.025 g |
| Magnesium stearate | 0.005 g |
| Hydrated silica | 0.010 g |

EXAMPLE 14 - Capsules

| | |
|---|---|
| Derivative No. 2 | 0.125 g |
| Magnesium stearate | 0.010 g |
| Talc | 0.005 g |

EXAMPLE 15 - Drops

| | |
|---|---|
| Derivative No. 1 | 3.0 g |
| Flavoured excipient q.s. to make | 30 ml |

EXAMPLE 16 - Injectable solution

| | |
|---|---|
| Derivative No. 2 | 0.100 g |
| Isotonic solution q.s. to make | 2 ml |

The composition according to this invention possesses anti-inflammatory and antalgic properties and has also an inhibiting activity on blood-platelet aggregation.

It is applicable to the treatment of painful inflammatory phenomena in rheumatology, neurology, traumatology and odontostomatology. It is also applicable to the treatment of disorders of the cerebral and peripheral circulatory system and prevents atheroma-induced thrombosis.

Having now described my invention what I claim as new and desire to secure by Letters Patent is:

1. Compound selected from the compounds of the formula

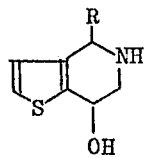 and 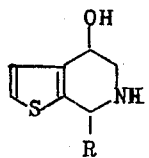

(I) and (II)

in which R is selected from the group consisting of hydrogen and the alkyl groups having 1–6 carbon atoms, and their therapeutically administrable acid addition salts.

2. 7-Hydroxy-4,5,6,7-tetrahydro-thieno[3,2-c]pyridine and its therapeutically administrable acid addition salts.

3. 4-Hydroxy-4,5,6,7-tetrahydro-thieno[2,3-c]pyridine and its therapeutically administrable acid addition salts.

4. 4-Hydroxy-7-methyl-4,5,6,7-tetrahydro-thieno[2,3-c]-pyridine and its therapeutically administrable acid addition salts.

5. 4-Hydroxy-7-ethyl-4,5,6,7-tetrahydro-thieno[2,3-c]-pyridine and its therapeutically administrable acid addition salts.

6. 7-Hydroxy-4-methyl-4,5,6,7-tetrahydro-thieno[3,2-c]-pyridine and its therapeutically administrable acid addition salts.

7. 7-Hydroxy-4-ethyl-4,5,6,7-tetrahydro-thieno[3,2-c]-pyridine and its therapeutically administrable acid addition salts.

8. Process for the preparation of a compound selected from the group consisting of the compounds of the formula:

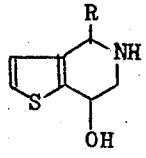 and 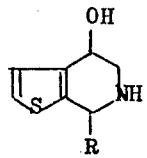

(I) and (II)

in which R is selected from the group consisting of hydrogen and the alkyl groups having 1–6 carbon atoms, and their acid addition salts, comprising cyclizing a compound selected from the group consisting of the compounds of the formula

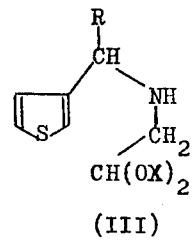 and (III) and

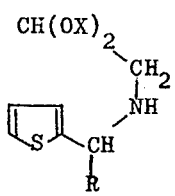

(IV), respectively, respectively, in which each X is individually selected from the lower alkyl groups and in which both X radicals may also form together a radical selected from the 2- and 3-membered alkylene radicals, by treatment with a strong acid at room temperature with stirring.

9. Process as claimed in claim 8, wherein said strong acid is hydrochloric acid.

10. Process as claimed in claim 8, wherein the compound selected from the compounds of the formula (III) and (IV) is prepared by reaction of a compound selected from 2- and 3-acyl-thiophenes with the acetal of the corresponding aminoacetaldehyde in which X is individually selected from the lower alkyl groups and in which both X radicals may also form together a radical selected from the 2- and 3-membered alkylene radicals, in a solvent selected from benzene and toluene under reflux, followed by hydrogenation of the resulting Schiff base in ethanol in the presence of NaBH$_4$ as reducing agent added first at room temperature and then under reflux.

* * * * *